United States Patent
Hewett

(10) Patent No.: US 7,674,224 B2
(45) Date of Patent: Mar. 9, 2010

(54) METHOD FOR INCORPORATING BRAIN WAVE ENTRAINMENT INTO SOUND PRODUCTION

(75) Inventor: Adam Hewett, Columbus, OH (US)

(73) Assignee: VitrePixel Holdings, LLC, Columbus, OH (US)

( * ) Notice: Subject to any disclaimer, the term of this patent is extended or adjusted under 35 U.S.C. 154(b) by 1153 days.

(21) Appl. No.: 11/251,051

(22) Filed: Oct. 14, 2005

(65) Prior Publication Data

US 2007/0084473 A1 Apr. 19, 2007

(51) Int. Cl.
*A61M 21/00* (2006.01)

(52) U.S. Cl. .................. 600/28; 600/544; 600/545

(58) Field of Classification Search ............. 600/26–28, 600/545, 544; 128/898; 381/312, 314; 434/238
See application file for complete search history.

(56) References Cited

U.S. PATENT DOCUMENTS

| | | | |
|---|---|---|---|
| 3,712,292 A | 1/1973 | Zentmeyer | |
| 4,141,344 A | 2/1979 | Barbara | |
| 4,191,175 A | 3/1980 | Nagle | |
| 4,227,516 A | 10/1980 | Meland et al. | |
| 4,315,502 A | 2/1982 | Gorges | |
| 4,777,529 A * | 10/1988 | Schultz et al. | ............... 348/484 |
| 5,135,468 A | 8/1992 | Meissner | |
| 5,213,562 A | 5/1993 | Monroe | |
| 5,289,438 A | 2/1994 | Gall | |
| 5,586,967 A | 12/1996 | Davis | |

* cited by examiner

*Primary Examiner*—Charles A Marmor, II
*Assistant Examiner*—Carrie Harris
(74) *Attorney, Agent, or Firm*—Venable, Campillo, Logan & Meaney, P.C.

(57) ABSTRACT

A method for incorporating brain wave entrainment into an audio composition by selectively modulating musical elements within the composition. The invention provides a way to specify and modulate individual frequency components in an audio composition, according to the desired brain wave state, allowing brain wave entrainment to be easily and subtly incorporated into an audio composition by disguising the modulations as natural instrumental qualities such as vibrato or reverberation.

20 Claims, 4 Drawing Sheets

METHOD FOR INCORPORATING BRAIN WAVE ENTRAINMENT INTO SOUND PRODUCTION

FIELD OF INVENTION

The present invention relates to a method of altering brain waves using sound patterns; more specifically, the invention relates to a method of controlling brain waves by altering specific parts of an audio composition.

BACKGROUND OF THE INVENTION

The electrical activity in the brain produces detectable signals known as brain waves, the frequency of which is associated with changes in mental state and cognitive ability. During daily waking life, a normal human brain functions at frequencies ranging from 13 to 25 Hertz (Hz), or cycles per second, called the beta state. During times of rest or daydreaming, brain wave cycles drop to 8 to 12 cycles per second, or the Alpha state. When sleeping, Theta and Delta states are dominant, ranging from 4 to 7 and 0.2 to 4 cycles per second respectively.

Brain waves can be altered if a person is presented with precisely timed, repetitive stimuli through the ears or eyes at repetition rates equal to the desired brain wave frequency. This is called brain wave entrainment. For example, if a 5 beat per second audio loop is played to a subject over a period of 6 minutes or more, the subject's brain will entrain to 5 cycles per second, or brain activity at the 5 Hz frequency will increase. FIG. 1A depicts a typical brain wave entraining beat with a pure tone. FIG. 1B shows a brain wave response to the beat. Because brain waves relate to mood and attention levels, researchers believe that stimulating frequencies can assist in a variety of activities, including relaxation, concentration, sleep and more.

Previous inventions have used flashing lights or pulsing tones to produce brain wave entrainment, as shown by U.S. Pat. Nos. 4,315,502 and 5,289,438.

However, pure tones and tone pulses can be quite invasive, grating and distracting to many people. Previous inventions have endeavored to solve this problem by masking over the entrainment with white noise, such as in U.S. Pat. No. 5,213,562, or music. Unfortunately, masking the brain wave entraining sounds of an audio composition can decrease the effectiveness of the brain stimulation. Additionally, while the masking acts to hide the harsh tones used, it does not eliminate them. Often the tones can still be heard distantly and can interfere with any added music or sounds.

Music alone has been used to affect the brain such as in U.S. Pat. No. 5,586,967, which describes a method and apparatus for inducing enhanced states of learning by presenting musical sounds in ascending and descending crescendos. Unfortunately the tempo of music stimulating brain waves is limited since brain wave frequencies range as high as 60 cycles per second.

Other methods have endeavored to tackle this problem by applying modulations non-specifically to entire pieces of music. Modulations alter sound to create a pattern of beats where none existed before. FIG. 2A depicts a sound file prior to modulation and FIG. 2B shows the same sound modulated to produce a brain wave entraining beat, using amplitude modulation. But the basic problem remains, since the only way to create subtle, non-invasive audio entrainment in this case is to decrease the intensity of the modulation, thus decreasing the overall effectiveness of the brain wave entrainment.

SUMMARY OF INVENTION

The invention is summarized below only for purposes of introducing embodiments of the invention. The ultimate scope of the invention is to be limited only to the claims that follow the specification.

The present invention solves the described problem by selectively modulating specific elements, or frequency components, of an audio composition, as opposed to modulating the whole of it or using the composition as a mask for underlying pure tones.

For example, the present invention can single out violins in an orchestra and modulate only that instrument type. Since certain instruments and musical compositions naturally contain modulations such as tremolo, vibrato, crescendos and reverberations, the end result, after modulation have been applied, will seem natural, as if the music always contained such modulations, but the effect of the brain wave entrainment will remain.

Further, the present invention allows the modulation of each element of an audio composition in specific ways. There are many types of modulations that work effectively to produce brain wave entrainment. Amplitude (volume) modulation is one type; frequency modulation, panning (in stereo sound), band pass filter modulation and other techniques can also be employed. Since each instrument has different characteristics, using a variety of modulations makes it possible to modulate all the elements of an audio composition in different ways while maintaining a natural-sounding piece of music.

Additionally, the present invention does not affect or rely on the tempo of the music, so it could be used to affect the brain in a manner contrary to the mood of the music. For example, an energizing beta state (13-25 cycles per second) could be promoted even if the audio composition being modulated is sedate in nature, or slow in tempo. This could be useful for double blind testing or in situations where a limited number of audio compositions are available.

In keeping with these objects and others which may become apparent, the present invention provides a method for applying brain wave entraining modulations individually to the various frequency components contained in an audio composition. Briefly, the method involves providing an audio composition, in either a pre-recorded format (such as a CD, tape or digital media file) or in a pre-synthesized form such as the MIDI format or in a programmable synthesizer. The method also provides a way to specify the frequency components (also described as instruments or elements) that will be affected by the modulations. The method further provides a way to specify the brain wave protocol, which determines the rate at which the selected frequency components will be modulated through the timeline of the composition. Finally, the method includes a way to mix the final output to create a cohesive audio composition that includes the embedded modulations in the selected frequency components.

Use of the words "function" or "means" in the specification and claims is not intended to indicate a desire to invoke the special provision of 35 U.S.C. §112, paragraph 6 to define the invention. To the contrary, if the provisions of 35 U.S.C. §112, paragraph 6 are sought to be invoked to define the invention(s), the claims will specifically state the phrases "means for" or "step for" and a function, without also reciting in such phrases any structure, material, or act in support of the function. Moreover, even if the provisions of 35 U.S.C. §112, paragraph 6 are invoked to define the inventions, it is intended that the inventions not be limited only to the specific structure, material or acts that are described in the preferred embodiments, but in addition, include any and all structures, materials or acts that perform the claimed function, along with any and all known or later developed equivalent structures, materials, or acts for performing the claimed function.

Further objects and advantages of the present invention will become apparent from the consideration of the drawings and ensuing description. The description of the invention that follows, together with the accompanying drawings, should not be construed as limiting the invention to the example shown and described, because those skilled in the art to which this invention pertains will be able to devise other forms thereof within the ambit of the appended claims.

DETAILED DESCRIPTION

Figure 1A:
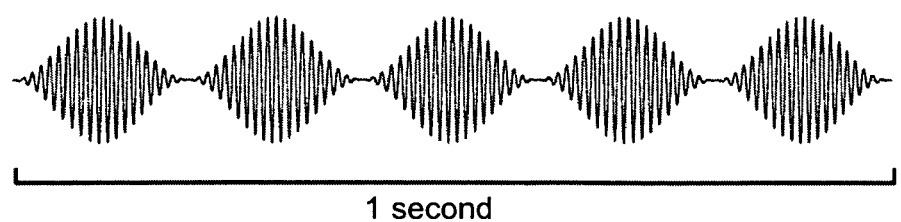
FIG. 1A—Depicts a sound pulse at 5 Hz.
Figure 1B:
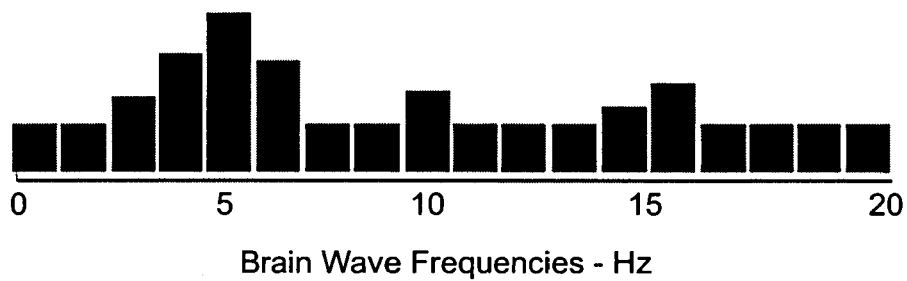
FIG. 1B—Depicts a brain wave pattern resulting from a sound pulse at 5 Hz.
Figure 2A:
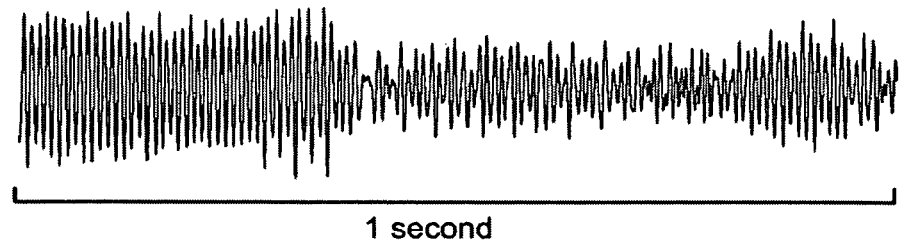
FIG. 2A—Depicts the wave form of a one second sound clip.
Figure 2B:
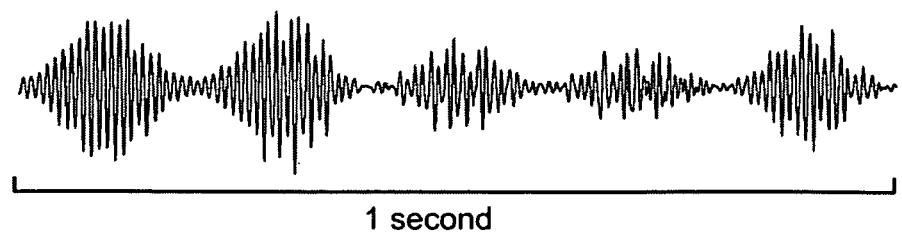
FIG. 2B—Depicts the sound clip of FIG. 2A after 5 Hz modulation has been applied.

It is to be understood that the descriptions below are merely illustrative of the presently preferred embodiments of the invention and that no limitations are intended to the detail of construction or design herein shown other than as defined in the appended claims.

Preferred Embodiment

Since much sound modification and synthesis is now done on a computer, the preferred embodiment of this invention is as a specially designed software program on a computer processor equipped with memory, interactive input (keyboard and mouse), audio input/output, speakers, and a conventional visual display. Optionally, the computer could interface with a sound synthesis device such as a keyboard or synthesizer, or could receive multiple inputs from a set of musical instruments via strategically placed microphones.

Band Pass Filtering

Band pass filtering is done programmatically through the software. A band pass filter is a conventional device or process that passes frequencies within a certain range and rejects frequencies outside that range. Software methods and code for this are readily available and should be well known by those versed in sound engineering. An existing program capable of Band Pass filtering is Audition 1.5 sold commercially by Adobe Systems, Inc.

Band Stop Filtering

Band stop filtering is done programmatically through the software. Also called a notch filter, t-notch filter, band-elimination filter, and band-rejection filter, this is a conventional audio process that passes most frequencies unaltered, but attenuates those in a range to very low levels. Software methods and code for this are readily available and should be well known by those versed in sound engineering. An existing program capable of Band Stop filtering is Audition 1.5 sold commercially by Adobe Systems, Inc.

Modulation

Modulation is also done programmatically through the software using a technique known as low frequency oscillation (LFO). LFO is an additional oscillator that operates at a lower frequency that modulates the audio signal, thus causing a difference to be heard in the signal without the actual introduction of another sound source. LFO is commonly used by electronic musicians to add vibrato or various effects to a melody. In this case it is used to modulate the amplitude, frequency, stereo panning or filters according to the brain wave protocol specified. Software methods and code for implementing LFO are readily available and should be well known by those versed in sound engineering. An existing program capable of LFO is Buzz distributed for free on Buzzmachines.com.

Brain Wave Protocol

A brain wave protocol is used to express the desired brain wave frequencies across the timeline of an audio composition. This can be represented using a chart with a time span represented horizontally and brain wave frequencies vertically. Desired frequencies can then be plotted across the timeline. The brain wave protocol is then used to control the rate of Modulation. For example, if the brain wave protocol is plotted to start at a desired brain wave of 15 cycles per second and then descend to 10 cycles per second over a 5 minute period, the Modulator will start at a rate of 15 modulations a second and slow that rate to 10 modulations a second over a 5 minute period. Software methods and code to plot a timeline in this fashion should be well known to anyone versed in computer programming. An example is a conventional spread sheet program like Excel, sold commercially by Microsoft, Inc.

Software Model

Figure 3:
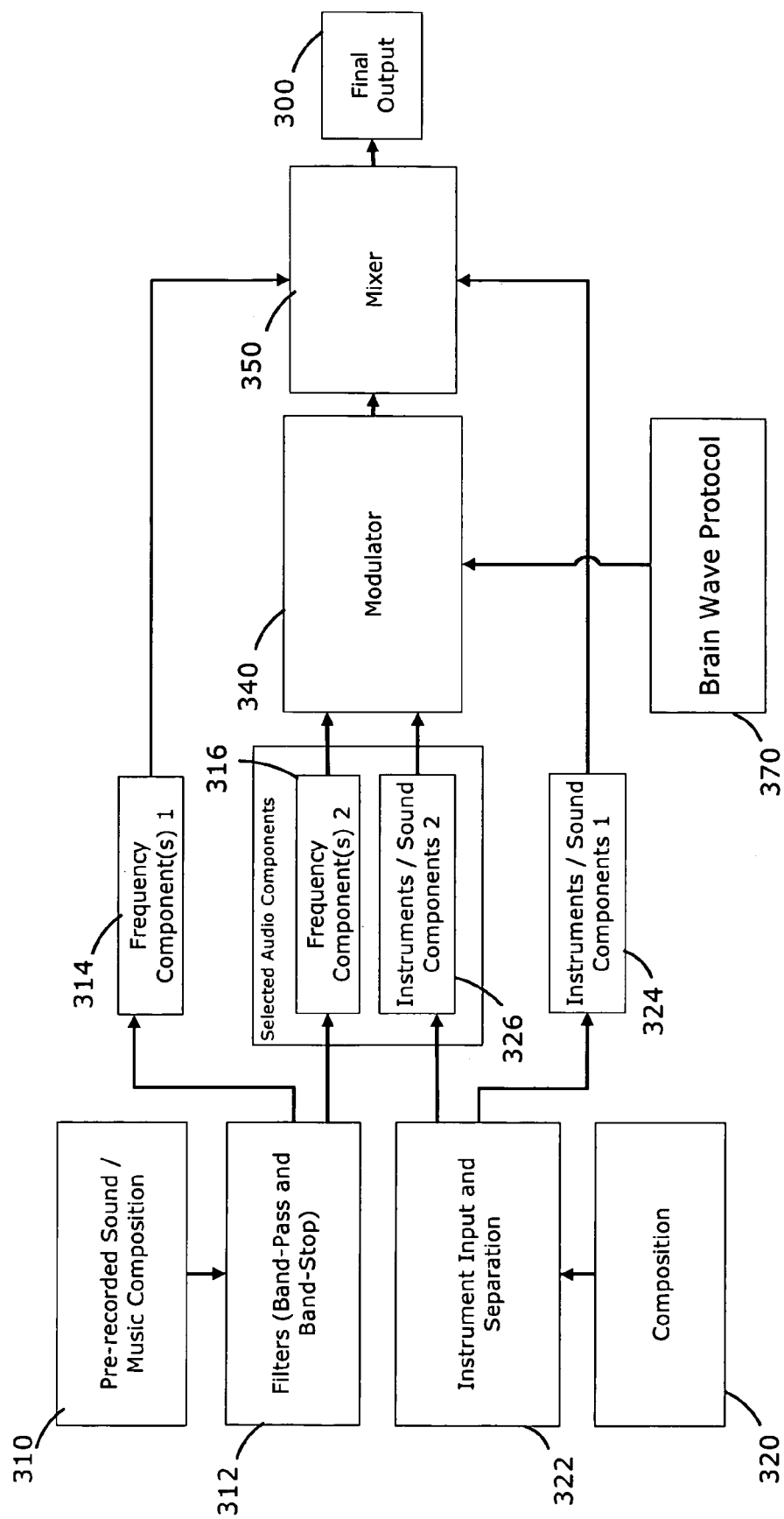
FIG. 3—A flow chart of a software system that may be used to separate and modulate individual frequency components according to a brain wave protocol.

FIG. 3 depicts a logical flow chart of the computer functions to be performed in accordance with the present invention. The computer programming can start in two places, either with a pre-recorded audio composition (310), or with an audio composition that is about to be recorded or synthesized (320).

Starting with the pre-recorded composition (310), the frequency components must be separated out so they can be selected by the user and modulated (340) or mixed (350) into the final output (300). To separate frequency components of a pre-recorded composition, a filter (312) must be employed. In this case the filter could be as simple as using a band pass to select a single frequency band (say from 400-500 Hz) or it could be as complex as a series of band-stop/notch filters used to separate instruments into their individual frequency components. In either case, frequency components can be selected for modulation (316), or can be excluded (314) and passed directly to the mixer (350). If selected for modulation, the selected frequency components (316) are passed to the modulator (340) where they are modulated using LFO techniques according to the brain wave protocol specified by the user (370). After the selected frequency components have been modulated, they are passed to the mixer (350) where they are rejoined with the remaining frequency components (314) and then passed to the final sound output (300).

Starting with a musical composition (320), such as sheet music, a MIDI file, or a programmed synthesizer, the instruments do not need an audio (band) filter but instead require a special input system, driver or configuration that will depend largely on the equipment used in the recording. Instrument Input and Separation (322) represents a means to separate the instruments or take input from multiple sources. After a set of instruments are selected for modulation (326) they are passed to the modulator which modulates in the same fashion as above, according to the brain wave protocol specified (370). The instruments are later mixed (350) with non-modulated instruments (324) and then passed to the final sound output (300).

Operation

Figure 4:
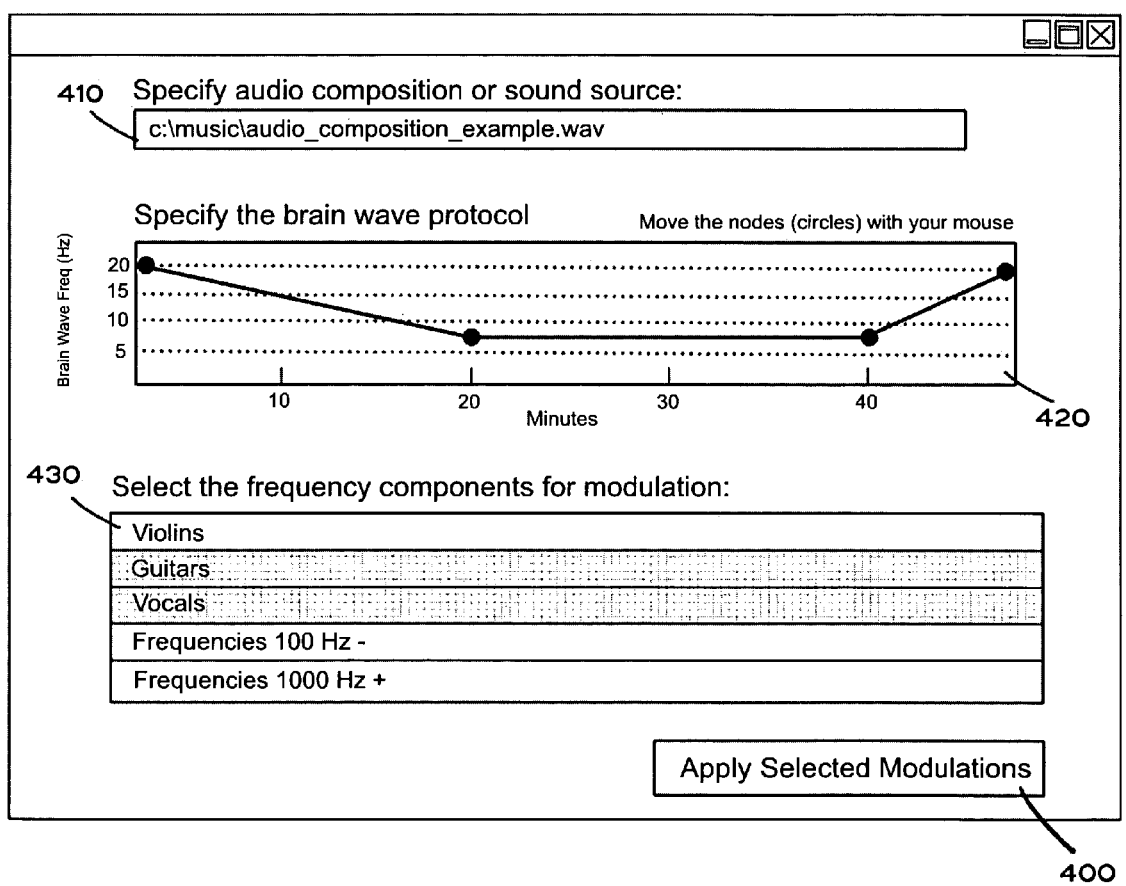
FIG. 4—An example of a visual display typical to the present invention.

FIG. 4 depicts an example software interface that could be used to operate a simple version of the present invention. An audio composition is provided (410), which can be any sound input from a digital media file to a sound generator or synthesizer. A brain wave protocol can be specified across the timeline of the audio composition by moving points across a chart representing the timeline (420) with mouse input. In FIG. 4, the timeline of composition is assumed to be about 50 minutes, represented horizontally while the desired brain wave frequency is represented vertically (420). Frequency components of the audio composition can be chosen according to instrument or frequency range (430). The modulations are then applied to the selected frequency range by clicking the "Apply Selected Modulations" button (400). Once done, the frequency components, both affected and unaffected by the modulations, are automatically mixed and the final sound output created. The final output could be played via speakers or exported to a digital audio file or media device.

Figure 5:
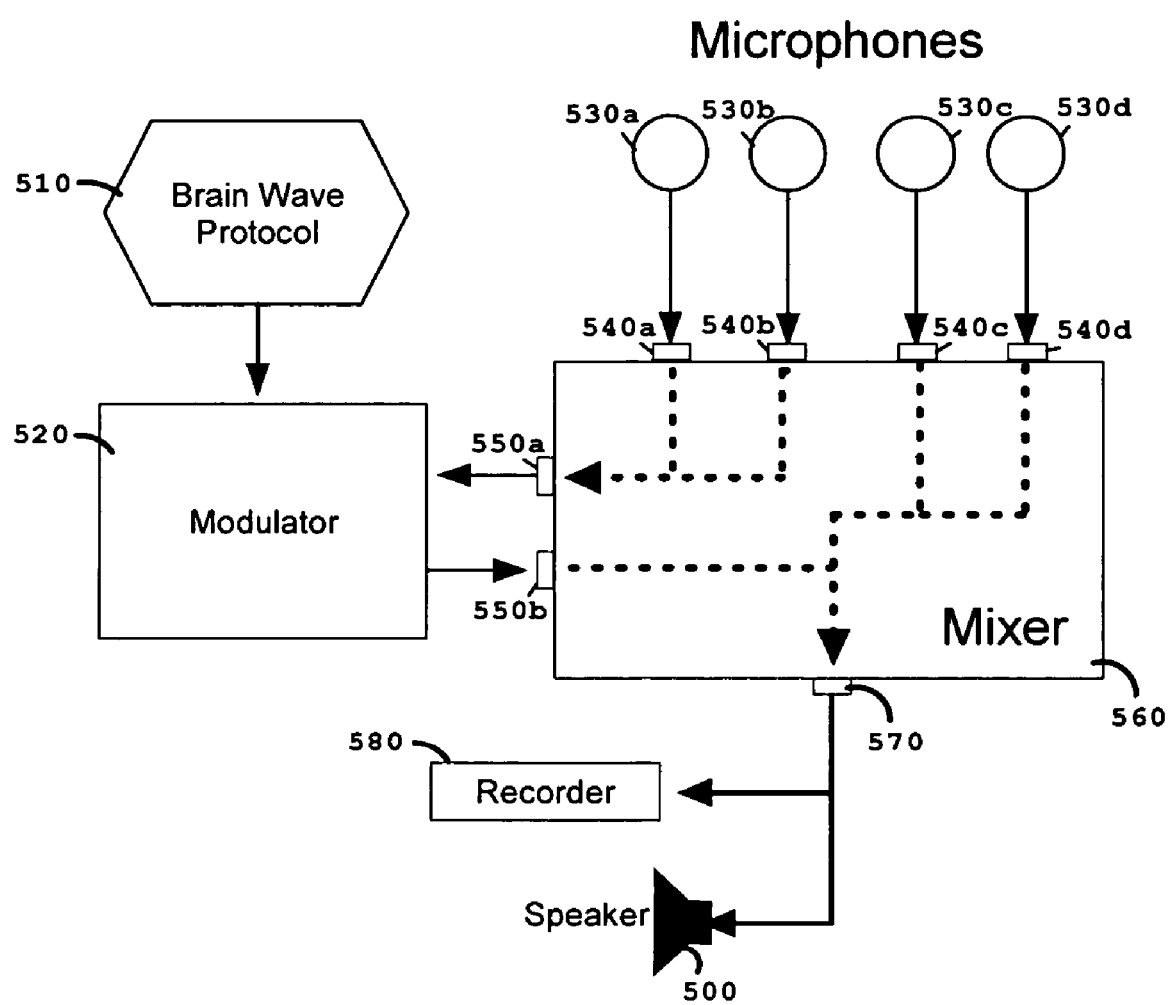
FIG. 5—A block diagram of an alternative system that may be used to take multiple microphone inputs and selectively modulate two of the inputs according to a brain wave protocol.

While the above description contains many specificities, these should not be construed as limitations on the scope of the invention, but rather as an exemplification of one preferred embodiment thereof. Many other variations are possible. For example, an alternative embodiment of this invention would be a hardware-based model meant for live music concerts or recording studios. FIG. 5 shows a conventional analog mixer (560) being used to route two microphones (530a and 530b) through the auxiliary sends/returns (550a send, 550b return) to a modulator (520) operating in accordance with a brain wave protocol (510). Microphones 530c and 530d are mixed with the modulated sound from the auxiliary return (550b), through the main output (570) to a conventional amplifier/speaker (500) and/or recorder (580).

Accordingly, the scope of the invention should be determined not by the embodiment(s) illustrated, but by the appended claims and their legal equivalents.

The invention claimed is:

1. A method for altering an audio composition for use in achieving brainwave states and stimulating the brain, comprising the acts of:
   a) selecting an audio composition, the audio composition comprising a plurality of frequency components;
   b) selecting a brainwave protocol, the brainwave protocol comprising the desired brain wave frequencies across a timeline of the audio composition;
   c) separating the audio composition into a plurality of signals, wherein the act of separating further comprises a filter;
   d) modulating at least one of the plurality of signals according to the selected brainwave protocol; and
   e) remixing the signals to produce a final output.

2. The method according to claim 1, wherein the audio composition is in digital format.
3. The method according to claim 1, wherein the act of separating further comprises a band pass filter.
4. The method according to claim 1, wherein the act of separating further comprises a band stop filter.
5. The method according to claim 1, wherein the plurality of frequency components are categorized by musical instrument.
6. The method according to claim 1, wherein the act of modulating further comprises amplitude modulation.
7. The method according to claim 1, wherein the act of modulating further comprises the act of stereo panning.
8. The method according to claim 1, wherein the act of modulating further comprises frequency modulation.
9. The method according to claim 1, wherein the final output is in digital audio format.
10. The method according to claim 1, wherein the brain wave protocol comprises a chart representing time horizontally and desired brain wave frequency vertically.
11. A method for altering an audio composition for use in achieving brainwave states and stimulating the brain, comprising the acts of:
    a) selecting an audio composition having a plurality of frequency components;
    b) selecting a brainwave protocol, the brainwave protocol comprising the desired brain wave frequencies across a timeline of the audio composition;
    c) separating the audio composition into a plurality of signals, wherein the act of separating further comprises a filter;
    d) modulating the filter parameters according to the brainwave protocol; and
    e) remixing the signals to produce a final output.
12. The method according to claim 11, wherein the act of separating further comprises a band pass filter.
13. The method according to claim 11, wherein the brain wave protocol comprises a chart representing time horizontally and brain wave frequency vertically.
14. A method for producing an audio composition for use in achieving brainwave states and stimulating the brain, comprising the acts of:
    a) generating a plurality of frequency components;
    b) selecting a brainwave protocol comprising brain wave frequencies across a timeline of the audio composition;
    c) modulating at least one of the plurality of frequency components using an audio modulator according to the brainwave protocol wherein at least one of the plurality of frequency components is modulated independently of the others; and
    d) mixing the modulated frequency components with the non-modulated frequency components into a final sound output.
15. The method according to claim 14, wherein the plurality of frequency components are categorized by musical instrument.
16. The method according to claim 14, wherein the act of modulating further comprises amplitude modulation.
17. The method according to claim 14, wherein the act of modulating further comprises the act of stereo panning.
18. The method according to claim 14, wherein the act of modulating further comprises frequency modulation.
19. The method according to claim 14, wherein the final output is in a digital audio format.
20. The method according to claim 14, wherein the brain wave protocol comprises a chart representing time horizontally and desired brain wave frequency vertically.

* * * * *